(12) United States Patent
Chen (10) Patent No.: US 9,770,054 B2
(45) Date of Patent: Sep. 26, 2017

(54) ELECTRONIC CIGARETTE

(71) Applicant: Shenzhen Smoore Technology Limited, Shenzhen (CN)

(72) Inventor: Zhiping Chen, Shenzhen (CN)

(73) Assignee: Shenzhen Smoore Technology Limited, Guangdong (CN)

(*) Notice: Subject to any disclaimer, the term of this patent is extended or adjusted under 35 U.S.C. 154(b) by 579 days.

(21) Appl. No.: 14/369,305

(22) PCT Filed: Mar. 27, 2014

(86) PCT No.: PCT/CN2014/074181
§ 371 (c)(1),
(2) Date: Jun. 27, 2014

(87) PCT Pub. No.: WO2015/143662
PCT Pub. Date: Oct. 1, 2015

(65) Prior Publication Data
US 2015/0272217 A1    Oct. 1, 2015

(51) Int. Cl.
*A24F 47/00* (2006.01)

(52) U.S. Cl.
CPC .................. *A24F 47/008* (2013.01)

(58) Field of Classification Search
CPC ........................................ A24F 47/00–47/008
USPC ............ 131/270–273, 194, 329; 128/202.21; 392/386, 324
See application file for complete search history.

(56) References Cited

U.S. PATENT DOCUMENTS

2011/0303231 A1* 12/2011 Li ..................... A24F 47/008
131/329

FOREIGN PATENT DOCUMENTS

| CN | 102326869 | * | 1/2012 | ............. A24F 47/00 |
| CN | 202890463 | * | 4/2013 | ............. A24F 47/00 |

OTHER PUBLICATIONS

CN 102326869 (Machine Translation) [online], [retrieved on Nov. 10, 2016], retrieved from ESPACENET (https://register.epo.org/advancedSearch?lng=en).*
CN 202890463 (Machine Translation) [online], [retrieved on Nov. 10, 2016], retrieved from ESPACENET (https://register.epo.org/advancedSearch?lng=en).*

* cited by examiner

*Primary Examiner* — Michael H Wilson
*Assistant Examiner* — Yana B Krinker
(74) *Attorney, Agent, or Firm* — Coats & Bennett, PLLC (57) ABSTRACT

An electronic cigarette includes: a housing; a mouthpiece located at one end of the housing, the mouthpiece defining an air outlet; a liquid reservoir received in the housing, the liquid reservoir defining a chamber for storing liquid and a channel communicated with the air outlet; a stopper located at an end of the liquid reservoir adjacent to the mouthpiece sealing the chamber; an atomizing assembly received in the housing and connected to the liquid reservoir, the atomizing assembly including a heating element configured to absorb the liquid and atomize the liquid into atomized gas; and a power source connected to the atomizing assembly, the power source being configured to provide power for the heating element. When refueling the liquid, a syringe needle can penetrate the stopper and inject the liquid into the cavity. Such injection procedure can be more conveniently performed without dissembling the liquid reservoir.

9 Claims, 6 Drawing Sheets

ELECTRONIC CIGARETTE

TECHNICAL FIELD

The present disclosure relates to electronic atomizers, and more particularly relates to an electronic cigarette.

BACKGROUND

Electronic cigarette, also known as virtual cigarette, electronic atomizers, is a substitute of the cigarette for smoking cessation. The electronic cigarette has a similar appearance and taste as the cigarette, while it generally contains no harmful ingredients of the cigarettes, such as tar, suspended particles, and so on.

A conventional electronic cigarette is usually composed of an atomizer and a battery to provide power to the atomizer. The atomizer usually includes a housing, a mouthpiece located on the top of the housing, an atomizing component received in the housing, and a liquid container for storing liquid. However, in the conventional electronic cigarette, when the liquid runs out, the liquid container can only be filled after disassembling the mouthpiece and replacing the atomizing component, which results in a higher cost. And the process of assembling a new atomizing component is very complicated.

SUMMARY

Accordingly, it is necessary to provide an electronic cigarette which is convenient to supple liquid.

An electronic cigarette includes:

a housing;

a mouthpiece located at one end of the housing, the mouthpiece defining an air outlet thereof;

a liquid reservoir received in the housing, the liquid reservoir defining a chamber for storing liquid and a channel communicated with the air outlet;

a stopper located at an end of the liquid reservoir adjacent to the mouthpiece sealing the chamber;

an atomizing assembly received in the housing and connected to the liquid reservoir, the atomizing assembly comprising a heating element configured to absorb the liquid and atomize the liquid into atomized gas; and a power source received in the housing and connected to the atomizing assembly, the power source being configured to provide power for the heating element.

In one embodiment, the liquid reservoir comprises a first tube and a second tube connected to the first tube, the chamber comprises a first cavity located in the first tube and a second cavity located in the second tube, an outer surface of the first tube and an inner surface of the housing form an air passage therebetween, the first tube is provided with a first plate at a bottom thereof, the first plate and an inner surface of the first tube form a first liquid passage therebetween, the second tube is provided with a second plate on a top thereof, the second tube is further provided with an air pipe connected to the second plate, the first plate and the second plate are spaced apart and arranged opposite to each other, the second plate and an inner surface of the second tube forms a second liquid passage therebetween, the liquid enters the second tube from the first tube via the first liquid passage and the second liquid passage, the channel comprises a first exhaust channel located in the air pipe and a second exhaust channel located between the first plate and the second plate, the first exhaust channel and the second exhaust channel are communicated with the air passage.

In one embodiment, the housing has a cylindrical shape, the second tube has a cylindrical shape matching the housing, the first tube has a cross-section shaped as a slotted hole, the number of the air passage is two, and two air passages are located at both sides of the first tube.

In one embodiment, the first plate has a rectangular shape, the number of the first liquid passage is two, and two first liquid passages are located at both sides of the first plate.

In one embodiment, the second plate is shaped as a slotted hole, the number of the second liquid passage is two, and two second liquid passages are located at both sides of the second plate.

In one embodiment, two straight sides of the second plate are respectively connected to two long sides of the first plate by two third plates; the second exhaust channel is formed by surrounding the first plate, the second plate, and the two third plates cooperatively.

In one embodiment, the atomizing assembly includes:

a fixing holder defining a through hole in a middle portion thereof, the fixing holder further defining two grooves on a side thereof, the two grooves being located at both sides of the through hole and communicated with the through hole;

the heating element comprising a liquid absorption element and a heating wire wound on the liquid absorption element, both ends of the liquid absorption element being received in the corresponding two grooves, and the heating wire being located in the through hole; and a guiding element received in the second tube, the guiding element comprising a main body and a guiding tube located at one side of the main body connected to the air pipe, wherein the guiding element defines a smoke guiding hole through the guiding tube and the main body, the main body resists the fixing holder, such that the heating element is positioned between the fixing holder and the guiding element, the heating element is aligned with the smoke guiding hole, the main body defines a notch, the liquid flows into the liquid absorption element from the second cavity via the notch.

In one embodiment, the guiding tube is made of elastic materials, a diameter of the guiding tube gradually decreases in a direction away from the main body, the guiding tube is inserted into the air pipe and is in close contact with an inner surface of the air pipe.

In one embodiment, the fixing holder comprises a base and a boss located at one side of the base, the two grooves are defined on the boss, the boss is threadedly fixed to the second tube, the base is threadedly fixed to the housing.

In one embodiment, the power source comprises a battery and a sensor located at an end of the battery, positive and negative electrodes of the battery are connected to both ends of the heating wire, the sensor is configured to turn the battery on or off.

When refueling the liquid, a needle of a syringe containing liquid can penetrate the stopper and enter the inside of the liquid reservoir, and the liquid can then be injected by the syringe into the cavity. Such injection procedure can be performed without dissembling the liquid reservoir, thus it is more convenient.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Reference will now be made to the drawings to describe, in detail, embodiments of the present electronic cigarette. It should be noted that references to "an" or "one" embodiment in this disclosure are not necessarily to the same embodiment, and such references mean at least one.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figure 1:
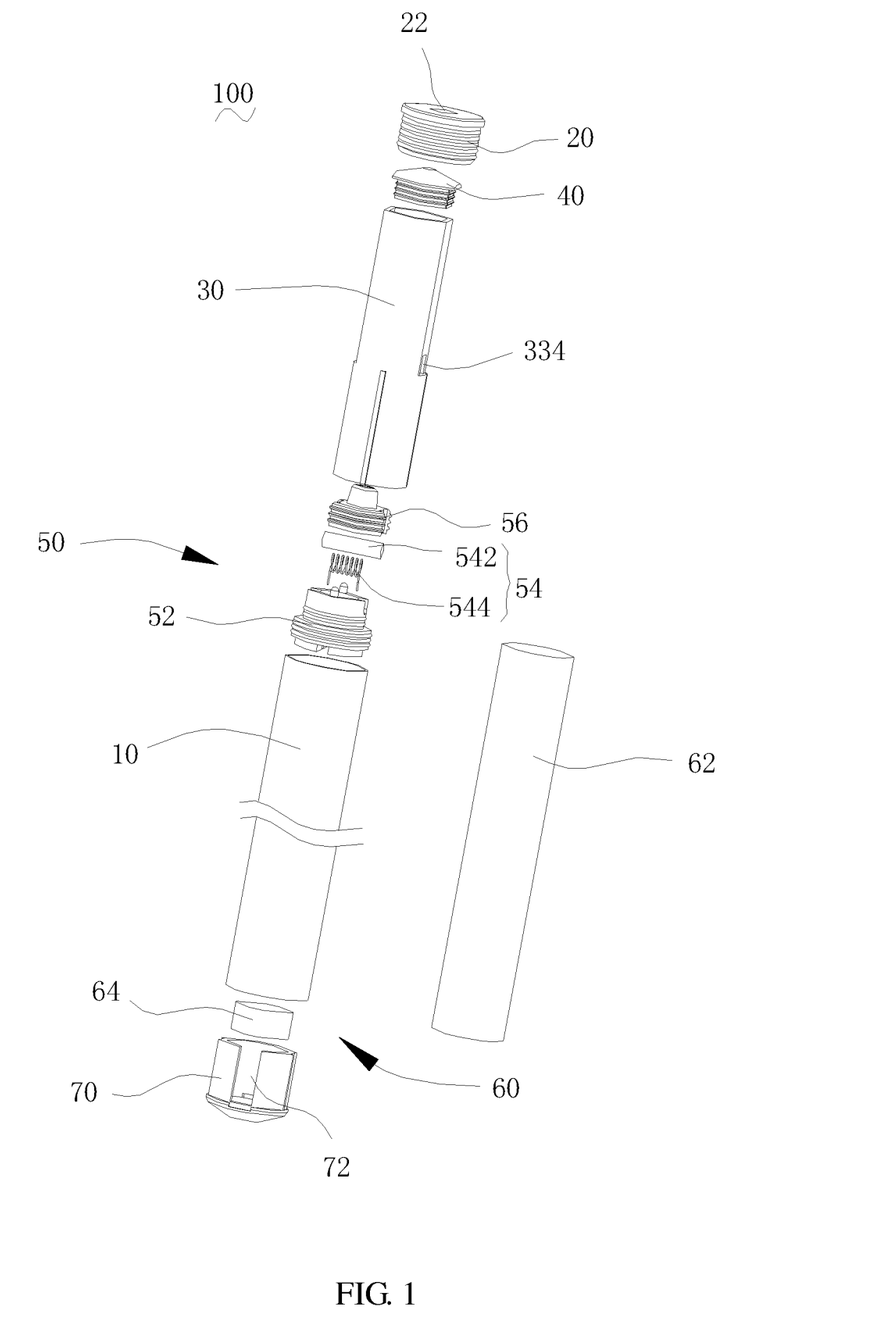
FIG. 1 is a disassembled perspective view of an embodiment of an electronic cigarette.

Referring to FIG. 1, an embodiment of an electronic cigarette 100 includes a housing 10, a mouthpiece 20, a liquid reservoir 30, a stopper 40, an atomizing assembly 50, a power source 60, and a cover 70.

The housing 10 is substantially a hollow elongated cylinder. The liquid reservoir 30, the stopper 40, the atomizing assembly 50, and the power source 60 are received in the housing 10, and the mouthpiece 20 and the cover 70 are located at both ends of the housing 10.

The mouthpiece 20 is provided with an outer thread and is threadedly fixed to an end of the housing. The mouthpiece 20 defines an air outlet 22 in a middle portion thereof.

Figure 2:
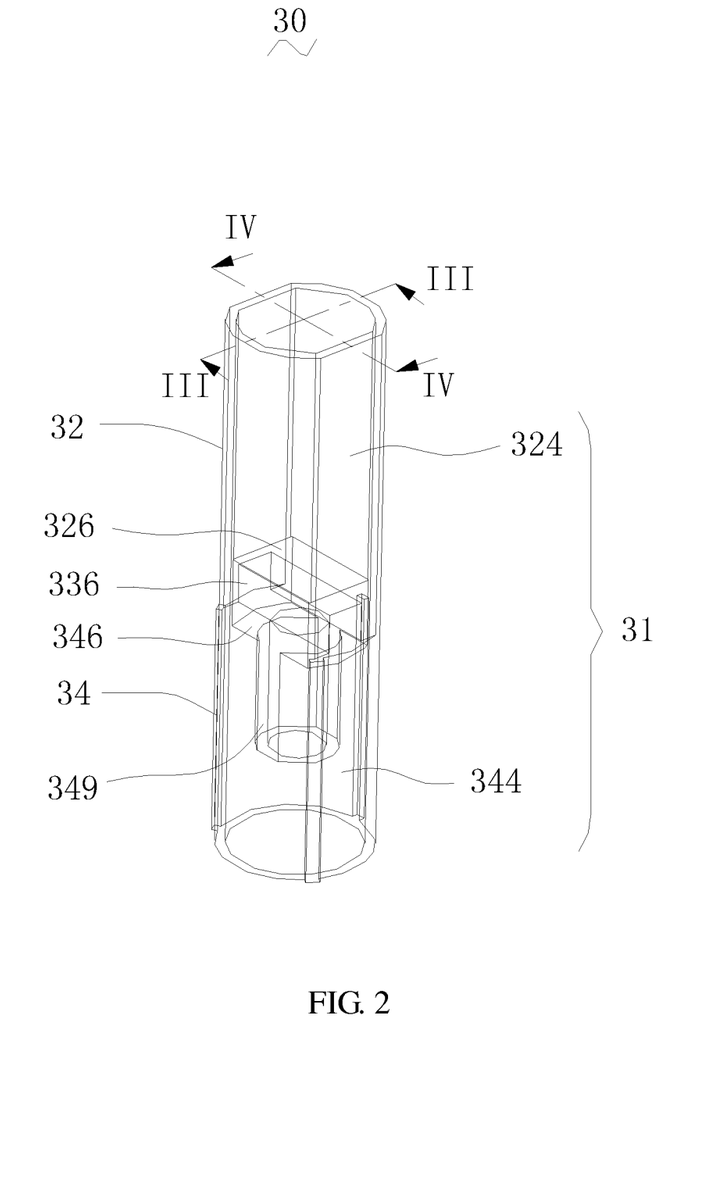
FIG. 2 is a perspective view of the electronic cigarette of FIG. 1.
Figure 3:
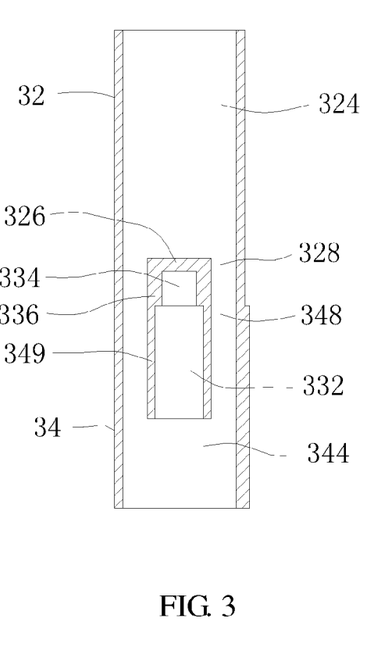
FIG. 3 is a cross-sectional view taken along line III-III of FIG. 2.
Figure 4:
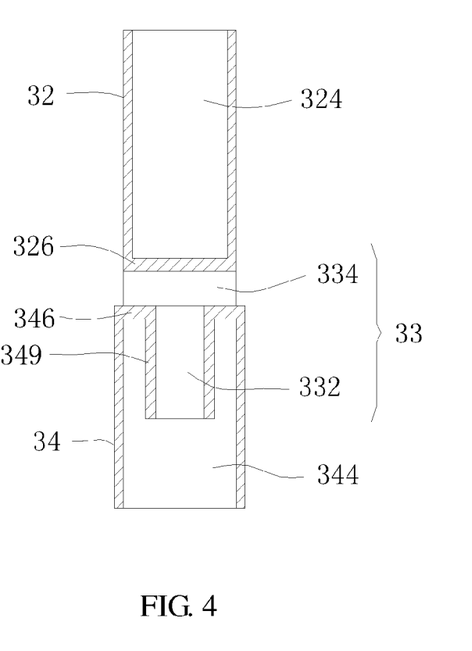
FIG. 4 is a cross-sectional view taken along line IV-IV of FIG. 2.

Referring to FIG. 2, FIG. 3 and FIG. 4, the liquid reservoir 30 is a substantially transparent elongated tube and internally defines a chamber 31 for storing liquid and a channel 33 for exhausting smoke. The liquid reservoir 30 includes a first tube 32 located on the top and a second tube 34 on the bottom. The first and second tubes 32, 34 are integrally formed. The cross-section of the first tube 32 has a shape of a slotted hole, which consists of two parallel lines straight lines and two arcs connected to both ends of the two straight lines, respectively. When the first tube 32 is received in the housing 10, two air passages 322 (see FIG. 7) are formed between two parallel sidewall of the first tube 32 and the two curved inner sidewalls of the housing 10. It should be understood that, in alternative embodiment, the cross-section of the first tube 32 may have other shape, such as triangle and the like. The number of the air passages 322 can be one, three, or more. The first tube 32 internally defines a first cavity 324 for storing liquid. The first tube 32 is provided with a first plate 326 located at the bottom of the first cavity 324. The first plate 326 is arranged perpendicular to an axis of the first tube 32. The first plate 326 is shaped as a substantially rectangle, and two short sides of the rectangle first plate 326 are connected to the two parallel sidewall of the first tube 32. Accordingly, two first liquid passages 328 are formed between two long sides of the rectangle first plate 326 and the two curved inner sidewalls of the first tube 32. The first liquid passage 328 has a substantially arched cross-section. It is to be understood that, in alternative embodiment, the number of the first liquid passage 328 can be one, three, or more.

The second tube 34 is substantially a hollow cylinder matching the housing 10, such that when the second tube 34 is received in the housing 10, an outer surface of the second tube 34 can be in close contact with the inner wall of the housing 10. The second tube 34 internally defines a second cavity 344 for storing liquid. The chamber 31 consists of the second cavity 344 and the first cavity 324. The second tube 34 is provided with a second plate 346 located on top of the second cavity 344. The second plate 346 is spaced and parallel to the first plate 326. The second plate 346 is shaped as slotted hole, and two arc-shaped sides of the second plate 346 are connected to the arc-shaped inner sidewall of the second tube 34, and two second liquid passages 348 are formed between two straight sides of the second plate 346 and the arc-shaped inner sidewall of the second tube 34. It should be understood that, in alternative embodiment, the number of the second liquid passage 348 can be one, three or more. The liquid flows from the first cavity 324 to the second cavity 344 via the first liquid passage 324 and the second liquid passage 348. The two straight sides of the second plate 346 are respectively connected to two long sides of the first plate 326 by two third plates 336. The first plate 326, the second plate 346, and the two third plates 336 surround and cooperatively form a second exhaust channel 334. The second exhaust channel 334 has two openings at both ends and is communicated with the two air passages 322 (see FIG. 7).

The second tube 34 further includes an air pipe 349 located beneath the second plate 346. The air pipe 349 is substantially a hollow cylinder and defines internally a first exhaust channel 332 which extends through the second plate 346. The first exhaust channel 332 is communicated with the second exhaust channel 334 and cooperatively forms the channel 33 with the second exhaust channel 334.

The stopper 40 is located at the top of the first tube 32 of the liquid reservoir 30. The first cavity 324 is sealed by the stopper 40. The stopper 40 is made of a material with a certain elasticity and density, such as silicone, rubber or other organic polymer materials. The stopper 40 can be easily penetrated by a needle or the like, and after the needle is withdrawn from the stopper 40, the liquid will not leak from the pinhole due to its elasticity.

Referring to FIG. 1 again, the atomizing assembly includes a fixing holder 52, a heating element 54, and a guiding element 56. The heating element 54 is mounted on the fixing holder 52. The guiding element 56, on the one hand, can guide the liquid to flow into the heating element 54, on the other hand, can guide to exhaust the smoke generated by the heat of the heating element 54.

Figure 5:
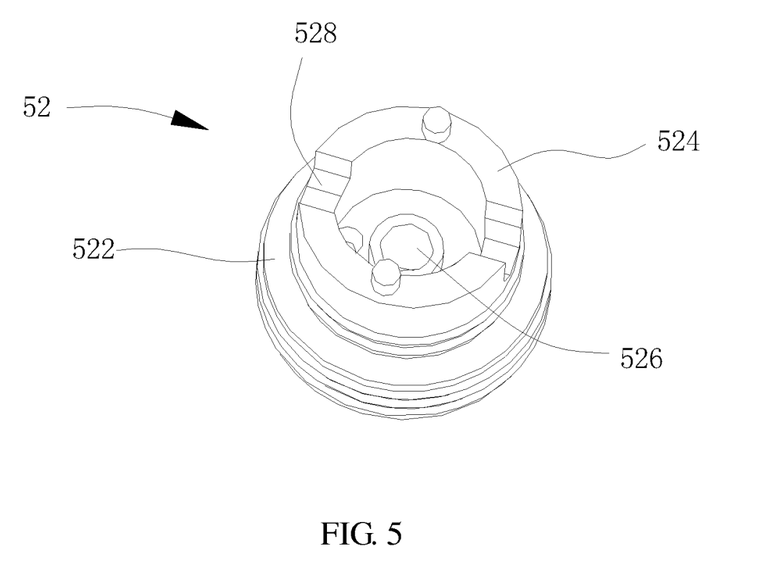
FIG. 5 is a perspective view of the fixing holder of FIG. 1.

Referring to FIG. 5, the fixing holder 52 includes a base 522 and a boss 524 located on the base 522. The base 522 is substantially disc-shaped, and the boss 524 is shaped substantially as ring. The fixing holder 52 defines a through hole 526 for exhausting the smoke in a middle portion thereof through the base 522 and the boss 524. The base 522 is provided with an external thread, by which the base 522 is threadedly fixed in the housing 10. The boss 524 defines two grooves 528 on the top thereof, the two grooves 528 are located at both sides of the through hole 526, each groove 528 is communicated with the through hole 526. The boss 524 is provided with an external thread, by which the boss 524 is threadedly fixed in the second tube 34 of the liquid reservoir 30. The fixing holder 52 is made of insulating materials, such as silicone, resin or ceramic and the like with heat resistance abilities.

Referring to FIG. 1 again, the heating element 54 includes a liquid absorption element 542 and a heating wire 544 wound on the liquid absorption element 542. The liquid absorption element 542 can be made of glass fiber or natural fiber with good liquid absorption abilities. Both ends of the liquid absorption element 542 are received in the two grooves 528, respectively, and the heating wire 544 is located in the through hole 526. The winding laps of the heating wire 544 may be three to eight, and the heating wire 544 may be nichrome wire.

Figure 6:
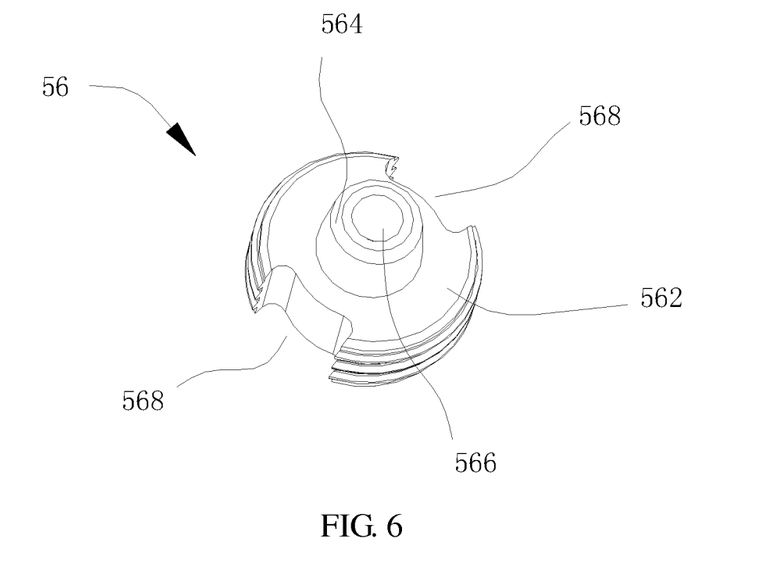
FIG. 6 is a perspective view of the guiding element of FIG. 1.

Referring to FIG. 6, the guiding element 56 includes a main body 562 and a guiding tube 564 located at a side of the main body 562. The guiding element 56 defines a smoke guiding hole 566 through the guiding tube 564 and the main body 562. The main body 562 has a disc-like shape. The bottom of the main body 562 resists the boss 524 of the fixing holder 52, such that the heating element 54 is firmly clamped between the fixing holder 52 and the guiding element 56. The main body 562 is threadedly fixed in the second tube 34. The main body 562 defines two opposing notches 568 at the edge thereof. Each notch 568 is aligned with one end of the liquid absorption element 542. Accordingly, the liquid can flow from the second cavity 344 to the liquid absorption element 542 via the notches 568. The guiding tube 564 is substantially tapered with a diameter gradually decreasing along a direction away from the main body 562, and the maximum diameter of the guiding tube 564 is greater than or equals to an inner diameter of the air pipe 349. The guiding tube 564 is made of elastic materials, such as silicon and the like. The guiding tube 564 can be inserted into the air pipe 349, such that the smoke in the guiding tube 564 can be guided into the air pipe 349. Since the guiding tube 564 is flexible, when it is inserted into the air pipe 349, the guiding tube 564 can be in close contact with the inner wall of the air pipe 349, thus preventing leak of smoke.

The power source 60 includes a batter 62 and a sensor 64. The battery 62 can be a lithium battery. The battery 62 is received in the housing 10, and positive and negative electrodes of the battery 62 are connected to both ends of the heating wire 544 via wires. The sensor 64 is located at one end of the battery 62 functioning as a switch, which can be used to turn on or turn off the battery 62.

The cover 70 is located at the end of the housing 10. An LED (not shown) can be provided inside the cover 70 to simulate the light of fire. The cover 70 defines an air inlet 72 in a middle portion thereof allowing the air to enter the electronic cigarette 100. It should be noted that, the cover 70 may be omitted.

Figure 7:
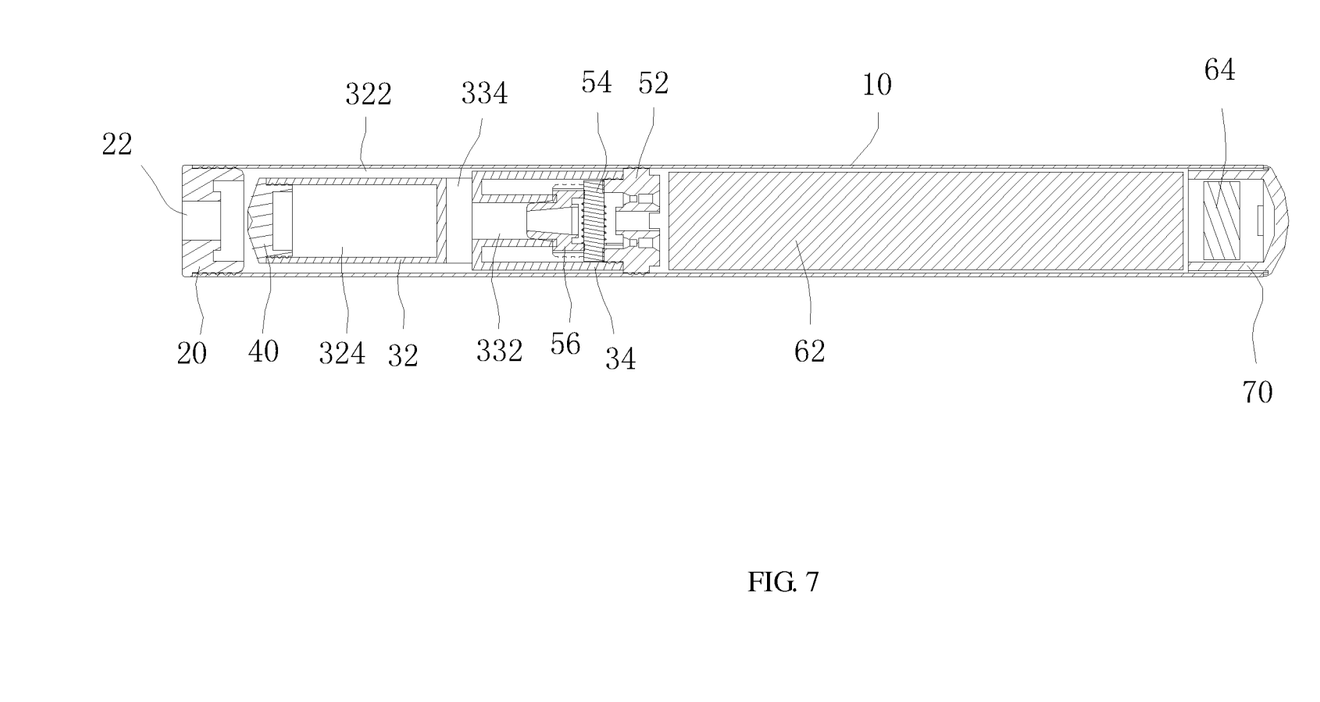
FIG. 7 is a cross-sectional view of the electronic cigarette of FIG. 1.
Figure 8:
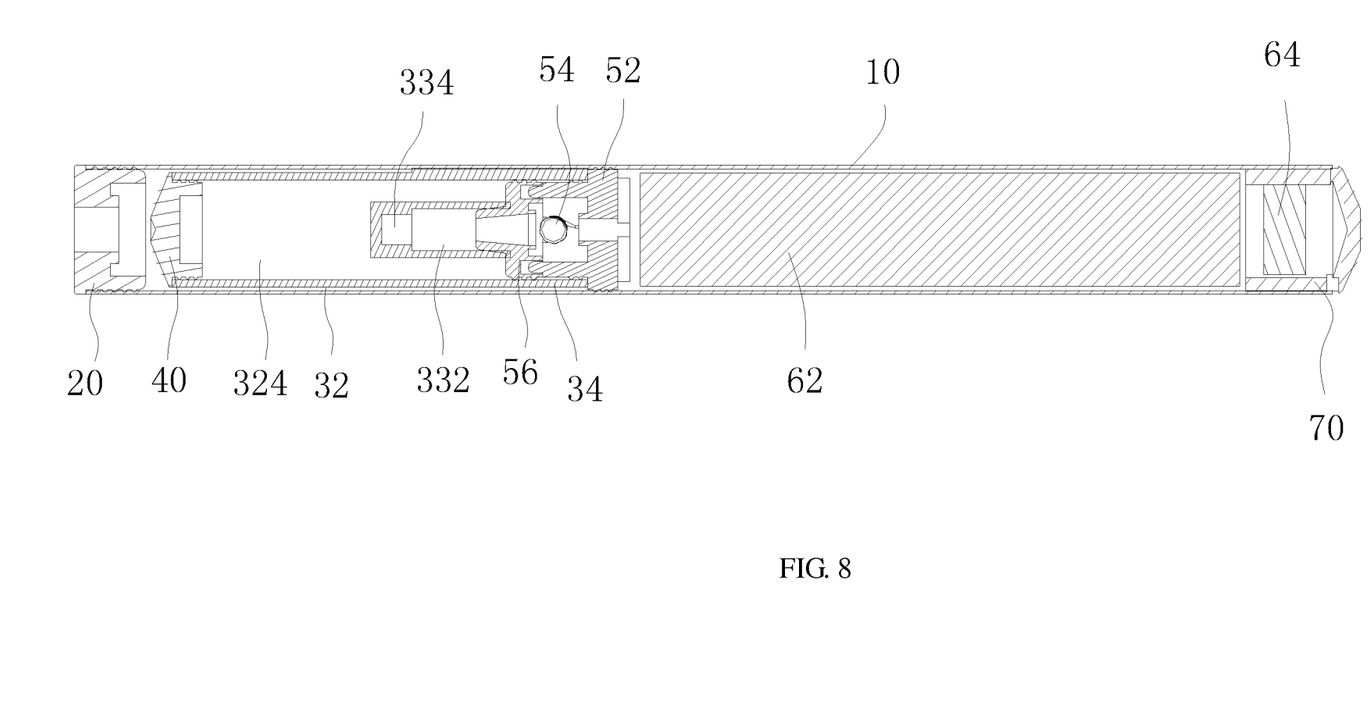
FIG. 8 is a cross-sectional view of the electronic cigarette of FIG. 1 viewed from another aspect.

Referring to FIG. 7 and FIG. 8, in assembly, the stopper 40 is mounted on top of the liquid reservoir 30, the guiding element 56 is then threadedly engaged in the liquid reservoir 30, and the guiding tube 564 is inserted in the air pipe 349. Next, the heating wire 544 is wound on the surface of the liquid absorption element 542, which is then mounted in the grooves 528 of the fixing holder 52. The fixing holder 52 is threadedly fixed to the bottom of the liquid reservoir 30, and the bottom of the liquid reservoir 30 resists the base 522. After that, the components described above are received in the housing 10 with the power source 60. After the mouthpiece 20 and the cover 70 are finally mounted to both ends of the housing, the assembly of the electronic cigarette 100 is completed.

When refueling the liquid, a needle of a syringe (not shown) containing liquid can penetrate the stopper 40 from the air outlet 22 of the mouthpiece 20 and enter the first cavity 324 of the liquid reservoir 30. The liquid can then be injected by the syringe into the first cavity 324. The liquid can flow from the first cavity 324 to the second cavity 344 via the first liquid passage 328 and the second liquid passage 348, then flow into the liquid absorption element 542 via the notch 568 until the liquid absorption element 542 is saturated. After the injection, the needle of the syringe is pulled out from the stopper 40, and the liquid will not leak from the pinhole due to the elasticity of the stopper 40. Such injection procedure can be performed without dissembling the liquid reservoir, thus it is more convenient.

In use, when the user inhales at the end of the electronic cigarette 100 having the air outlet 22, the air enters the electronic cigarette 100 from the air inlet 72. The liquid is vaporized into smoke by the heat of the heating element 544. The smoke is finally inhaled into the user's mouth through the through hole 526, channel 33, air passages 322, and the air outlet 22.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. An electronic cigarette, comprising:
   a housing;
   a mouthpiece located at one end of the housing, the mouthpiece defining an air outlet thereof;
   a liquid reservoir received in the housing, the liquid reservoir defining a chamber for storing liquid and a channel communicated with the air outlet;
   a stopper located at an end of the liquid reservoir adjacent to the mouthpiece sealing the chamber;
   an atomizing assembly received in the housing and connected to the liquid reservoir, the atomizing assembly comprising a heating element configured to absorb the liquid and atomize the liquid into atomized gas; and
   a power source received in the housing and connected to the atomizing assembly, the power source being configured to provide power for the heating element;
   wherein the liquid reservoir comprises a first tube and a second tube connected to the first tube, the chamber comprises a first cavity located in the first tube and a second cavity located in the second tube, an outer surface of the first tube and an inner surface of the housing form an air passage therebetween, the first tube is provided with a first plate at a bottom thereof, the first plate and an inner surface of the first tube form a first liquid passage therebetween, the second tube is provided with a second plate on a top thereof, the second tube is further provided with an air pipe connected to the second plate, the first plate and the second plate are spaced apart and arranged opposite to each other, the second plate and an inner surface of the second tube forms a second liquid passage therebetween, the liquid enters the second tube from the first tube via the first liquid passage and the second liquid passage, the channel comprises a first exhaust channel located in the air pipe and a second exhaust channel located between the first plate and the second plate, the first exhaust channel and the second exhaust channel are communicated with the air passage.

2. The electronic cigarette according to claim 1, wherein the housing has a cylindrical shape, the second tube has a cylindrical shape matching the housing, the first tube has a cross-section shaped as a slotted hole, the number of the air passage is two, and two air passages are located at both sides of the first tube.

3. The electronic cigarette according to claim 2, wherein the first plate has a rectangular shape, the number of the first liquid passage is two, and two first liquid passages are located at both sides of the first plate.

4. The electronic cigarette according to claim 3, wherein the second plate is shaped as a slotted hole, the number of the second liquid passage is two, and two second liquid passages are located at both sides of the second plate.

5. The electronic cigarette according to claim 4, wherein two straight sides of the second plate are respectively connected to two long sides of the first plate by two third plates; the second exhaust channel is formed by surrounding the first plate, the second plate, and the two third plates cooperatively.

6. The electronic cigarette according to claim 1, wherein the atomizing assembly comprises:
    a fixing holder defining a through hole in a middle portion thereof, the fixing holder further defining two grooves on a side thereof, the two grooves being located at both sides of the through hole and communicated with the through hole;
    the heating element comprising a liquid absorption element and a heating wire wound on the liquid absorption element, both ends of the liquid absorption element being received in the corresponding two grooves, and the heating wire being located in the through hole; and
    a guiding element received in the second tube, the guiding element comprising a main body and a guiding tube located at one side of the main body connected to the air pipe, wherein the guiding element defines a smoke guiding hole through the guiding tube and the main body, the main body resists the fixing holder, such that the heating element is positioned between the fixing holder and the guiding element, the heating element is aligned with the smoke guiding hole, the main body defines a notch, the liquid flows into the liquid absorption element from the second cavity via the notch.

7. The electronic cigarette according to claim 6, wherein the guiding tube is made of elastic materials, a diameter of the guiding tube gradually decreases in a direction away from the main body, the guiding tube is inserted into the air pipe and is in close contact with an inner surface of the air pipe.

8. The electronic cigarette according to claim 6, wherein the fixing holder comprises a base and a boss located at one side of the base, the two grooves are defined on the boss, the boss is threadedly fixed to the second tube, the base is threadedly fixed to the housing.

9. The electronic cigarette according to claim 6, wherein the power source comprises a battery and a sensor located at an end of the battery, positive and negative electrodes of the battery are connected to both ends of the heating wire, the sensor is configured to turn the battery on or off.

* * * * *